(12) United States Patent
Varesi (10) Patent No.: US 7,841,227 B2
(45) Date of Patent: Nov. 30, 2010

(54) DEVICE FOR PASSING THROUGH A GAS MIXTURE

(75) Inventor: Andreas Varesi, Munich (DE)

(73) Assignee: MEMBRANOTEC GmbH & Co. KG, Bremen (DE)

( * ) Notice: Subject to any disclaimer, the term of this patent is extended or adjusted under 35 U.S.C. 154(b) by 251 days.

(21) Appl. No.: 12/126,557

(22) Filed: May 23, 2008

(65) Prior Publication Data
US 2008/0282773 A1    Nov. 20, 2008

Related U.S. Application Data

(63) Continuation of application No. PCT/EP2006/011204, filed on Nov. 22, 2006.

(51) Int. Cl.
*G01N 7/10* (2006.01)
*B01D 53/22* (2006.01)

(52) U.S. Cl. .......................... 73/31.07; 96/4

(58) Field of Classification Search ............. 73/31.05, 73/31.07; 969/4, 6, 7, 8, 10
See application file for complete search history.

(56) References Cited

U.S. PATENT DOCUMENTS

| 3,415,038 | A | * | 12/1968 | Merten et al. .............. 95/53 |
| 4,658,636 | A | * | 4/1987 | Manning et al. .......... 73/54.07 |
| 5,316,568 | A |   | 5/1994 | Brown |
| 5,395,425 | A |   | 3/1995 | Brown |
| 5,469,732 | A |   | 11/1995 | Voss |
| 6,386,016 | B1 |  | 5/2002 | Gleissle |
| 7,115,881 | B2 | * | 10/2006 | Rabinowitz et al. ..... 250/423 R |
| 7,690,241 | B2 | * | 4/2010 | Muntz et al. ............. 73/31.07 |
| 2004/0048365 | A1 | | 3/2004 | Huie et al. |
| 2008/0223795 | A1 | * | 9/2008 | Bakajin et al. ............ 210/767 |

FOREIGN PATENT DOCUMENTS

| DE | 43 16 196 | 10/1993 |
| GB | 1271811 | 4/1972 |
| JP | 02 132371 | 5/1990 |

OTHER PUBLICATIONS

Peter Hänggi, Fabio Marchesoni and Franco Nori, "Brownian motors", Ann. Phys. (Leipzig) 14, No. 1-3, pp. 51-70, 2005.
Gopinath Bhimarasetti et al., "Carbon microtubes: tuning and internal diameters and conical angles", Nanotechnology, vol. 16, No. 7, Jul. 1, 2005, pp. S362-S369, Institute of Physics Publishing, Bristol, GB.
PCT Search Report dated Jun. 19, 2007.

* cited by examiner

*Primary Examiner*—Lisa M Caputo
*Assistant Examiner*—Punam Roy
(74) *Attorney, Agent, or Firm*—Patterson & Sheridan, LLP (57) ABSTRACT

A device for passing through a gas mixture comprises a capillary apparatus with one or more capillaries connecting a first side of the capillary apparatus to a second side of the capillary apparatus, wherein each capillary tapers from one side towards the other side of the capillary apparatus at least in sections.

20 Claims, 5 Drawing Sheets

DEVICE FOR PASSING THROUGH A GAS MIXTURE

CROSS-REFERENCE TO RELATED APPLICATIONS

This application is a continuation of co-pending PCT patent application No. PCT/EP2006/011204, filed 22 Nov. 2006, which claims the benefit of German patent application serial number DE 10 2005 055 675.2-52, filed 23 Nov. 2005. Each of the aforementioned related patent applications is herein incorporated by reference in its entirety.

BACKGROUND OF THE INVENTION

1. Field of the Invention

Embodiments of the present invention relate to a device and a method for passing through a gas mixture.

2. Description of the Related Art

The qualitative and quantitative analysis of the composition of gas mixtures plays an important role in many fields of technology. In the simplest case, detectors are used to detect the presence or the partial pressure of a single predetermined gas or of a gas from a predetermined group of gases in the gas mixture. Some gases can be detected using relatively simple and cost-effective detectors due to their chemical and/or physical properties, for example oxygen. Other gases, on the other hand, can be detected only using relatively complex and expensive detectors. Examples of this are the noble gases due to their chemically inert behavior. Detectors or detecting instruments for helium, by way of example, comprise mass spectrometers and cost at least approximately C1,000.00.

The extraction or enrichment of gases, for example of noble gases such as argon or helium, yields big profits around the world. The process of enriching or separating the desired gases from gas mixtures is based on different chemical or physical properties and is generally associated with high technical outlay and consumption of large amounts of energy.

SUMMARY OF THE INVENTION

One embodiment of the invention includes a device for passing through a gas mixture. The device may generally comprise: a capillary apparatus with one or more capillaries connecting a first side of the capillary apparatus to a second side of the capillary apparatus, wherein each capillary tapers from one side towards the other side of the capillary apparatus at least in sections.

Another embodiment of the invention includes a detector device for qualitatively or quantitatively detecting the presence of a predetermined gas in a gas mixture. The device may generally comprise: a capillary apparatus with one or more capillaries connecting a first side of the capillary apparatus to a second side of the capillary apparatus, wherein each capillary tapers from one side towards the other side of the capillary apparatus at least in sections; and a pressure detector connected to the second side.

Another embodiment of the invention includes a gas enrichment device for extracting a predetermined gas from a gas mixture or for enriching the predetermined gas. The device may generally comprise: a capillary apparatus with one or more capillaries connecting a first side of the capillary apparatus to a second side of the capillary apparatus, wherein each capillary tapers from one side towards the other side of the capillary apparatus at least in sections; a gas supply line for supplying the gas mixture, wherein the gas supply line is connected to one of the sides of the capillary apparatus; and a gas discharge line for removing the predetermined gas or a gas mixture in which the predetermined gas is enriched, wherein the gas discharge line is connected to the other side of the capillary apparatus.

Still another embodiment of the invention includes a device for generating mechanical power. The device may generally comprise: a capillary apparatus with one or more capillaries connecting a first side of the capillary apparatus to a second side of the capillary apparatus, wherein each capillary tapers from one side towards the other side of the capillary apparatus at least in sections; and a device for depressurizing gas and for generating mechanical power, wherein the entry side of the device is connected to one of the sides of the capillary apparatus, and wherein the exit side of the device is connected to the other side of the capillary apparatus.

Still another embodiment of the invention includes a device for inducing a rotational movement. The device may generally comprise: a shaft; and a capillary apparatus with one or more capillaries connecting a first side of the capillary apparatus to a second side of the capillary apparatus, wherein each capillary tapers from one side towards the other side of the capillary apparatus at least in sections; and wherein the capillary apparatus is connected to the shaft such that the axis of the shaft is approximately parallel to the first side and/or the second side.

Still another embodiment of the invention includes a method for passing through a gas mixture. The method may generally comprise: supplying a gas mixture to an inlet of a capillary, wherein the capillary is tapered in at least one section, such that the predetermined gas passes through the capillary at a predetermined flow rate.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Embodiments of the present invention provide a simple detector device for qualitatively or quantitatively detecting the presence of a predetermined gas in a gas mixture. Further, embodiments of the present invention provide a gas production device for extracting or enriching a predetermined gas from a gas mixture. Furthermore, embodiments of the present invention provide a device for at least temporarily outputting mechanical power and to provide a device for inducing a rotational movement.

Embodiments of the present invention are based on the concept of using a capillary apparatus with capillaries which taper from one side of the capillary apparatus towards the other side of the capillary apparatus at least in sections. Different gases flow in various ways through a capillary which tapers in one direction. In particular monatomic gases, or gases comprising single atoms (in particular noble gases), behave differently than molecular gases which comprise molecules of in each case two or more atoms (for example nitrogen, oxygen, water vapor etc.). Monatomic gases flow through the capillary faster than molecular gases, although here the atomic mass of the monatomic gas and the molecular mass of the molecular gas also have some influence.

According to one embodiment, the tapering capillaries are traversed in particular by monatomic gases and alternatively also by molecular gases faster, or at a higher rate, in one direction than in the opposite direction.

One side of the capillary apparatus is exposed to the gas mixture to be investigated by, for example, connecting this side of the capillary apparatus to a container in which the gas mixture is present via a gas line. The other side of the capillary apparatus is connected to a pressure detector which, in the simplest case, is formed in a riser pipe by way of a drop of glycerol or another liquid. Since different gases on the capillary apparatus exhibit different behaviors, and in particular traverse the capillary at different rates, the pressure detected at the pressure detector allows conclusions as to the gas composition to be drawn.

According to further embodiments of the present invention, the capillary apparatus is used to extract or enrich a predetermined gas from a gas mixture, to generate mechanical power and to induce a rotational movement. The rotational movement can be used, for example, for the detection and/or indication of the gas composition or of the partial pressure of the predetermined gas in the gas mixture.

Figure 1:
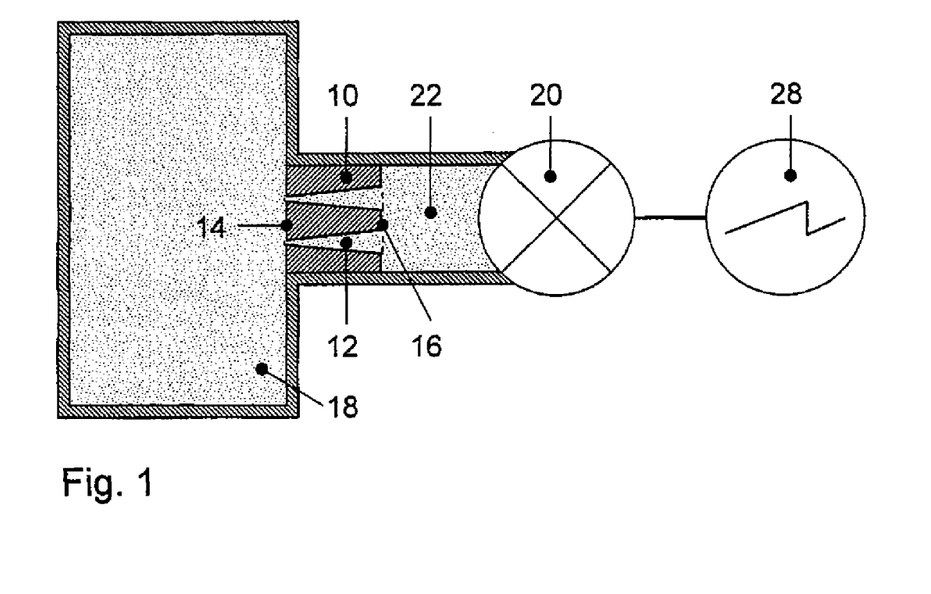
FIG. 1 shows a schematic illustration of a detector device, according to one embodiment of the invention.

FIG. 1 is a schematic illustration of a detector device comprising a capillary apparatus 10 and a pressure detector 20, according to one embodiment of the invention. The capillary apparatus 10 has one or a plurality of capillaries 12 which each connects a first side 14 of the capillary apparatus to a second side 16 of the capillary apparatus 10. The first side 14 of the capillary apparatus 10 is connected to a gas container 18 or another volume in which the gas mixture to be investigated is present. The pressure detector 20 is connected to the second side 16 of the capillary apparatus 10 via a line 22.

The capillaries 12 taper from the second side 16 towards the first side 14 of the capillary apparatus 10, i.e. the cross-sectional area of each capillary 12 increases from the first side 14 to the second side 16 of the capillary apparatus 10. FIG. 1, just like FIGS. 2 to 4 described below, shows schematic and not-to-scale illustrations. In particular, the capillaries 12 and their lateral dimensions may not be illustrated to scale. The minimum cross-sectional area which, in the example of FIG. 1, is by or near the first side 14 of the capillary apparatus 10, may have a dimension which is smaller at least in one direction than the twentyfold mean free path of the predetermined gas which is intended to be detected by the detector device at the designated measurement conditions (in particular overall pressure and temperature). Alternatively, the minimum cross-sectional area may have, in at least one direction, a dimension which is of the same order of magnitude as the mean free path, and in particular may be at most twice as large as the mean free path. In another embodiment, deviating from the illustration in FIG. 1, the capillaries 12 may taper alternatively from the first side 14 towards the second side 16 of the capillary apparatus 10. Other embodiments of the capillaries 12 will be explained in more detail below with reference to FIG. 3.

The pressure detector 20 is effectively connected to an evaluation apparatus 28 which receives a measurement signal from the pressure detector 20. The evaluation apparatus 28 is configured to generate an output signal on the basis of the measurement signal received by the pressure detector 20, which output signal indicates whether the predetermined gas is present in the gas mixture at a minimum concentration. Alternatively, the output signal may indicate the partial pressure or the proportion by volume or material of the predetermined gas in the gas mixture or a corresponding variable that quantifies the proportion of the predetermined gas in the gas mixture.

Figure 2:
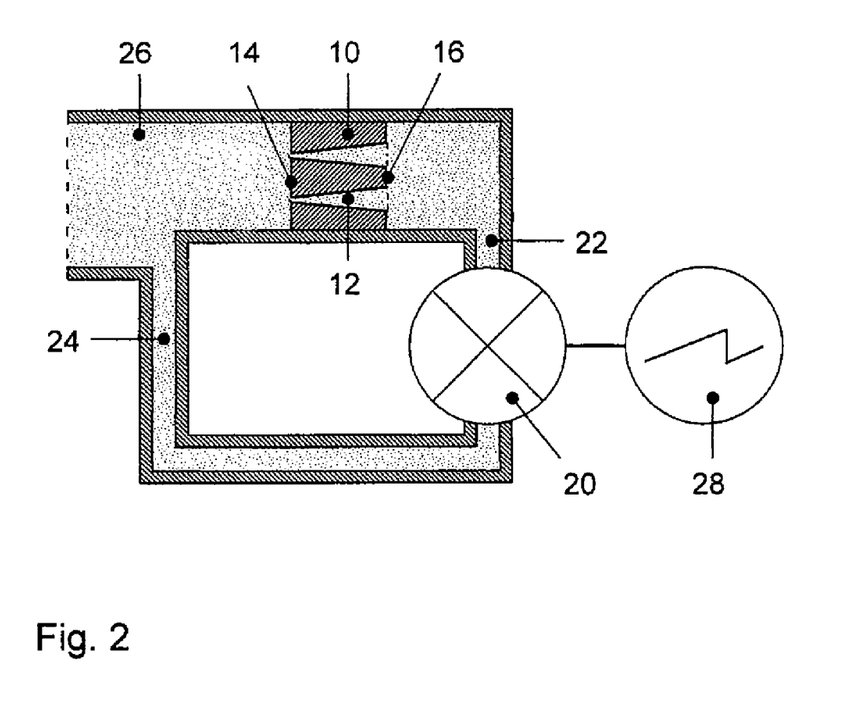
FIG. 2 shows a schematic illustration of another detector device, according to one embodiment of the invention.

FIG. 2 is a schematic illustration of a detector device in which the pressure detector 20 is a differential pressure detector for detecting a pressure difference, according to one embodiment of the invention. The pressure detector 20 is here connected to the first side 14 of the capillary apparatus 10 via a first line 24, and is connected to the second side 16 of the capillary apparatus 10 via a second line 22 in order to detect a pressure difference between the first side 14 and the second side 16 of the capillary apparatus 10. The first side 14 of the capillary apparatus 10 is furthermore connected, via another line 26, to a gas volume or gas container (not illustrated here) in which the gas mixture to be investigated is present. Similar to the detector device illustrated in FIG. 1, the pressure detector 20 is also connected to an evaluation apparatus 28.

Similar to FIG. 1, the other line 26 can, in deviation from the illustration of FIG. 2, be dispensed with by connecting the first side 14 of the capillary apparatus 10 directly to the gas volume, or by the first side 14 of the capillary apparatus 10 directly adjoining the gas volume. In such cases, the pressure detector 20 may be, in deviation from the illustration in FIG. 2, connected via the first line 24 or directly to the gas volume.

In another embodiment, deviating from the illustration in FIG. 2, the capillaries 12 may alternatively taper from the first side 14 towards the second side 16 of the capillary apparatus 10. In other embodiments, the capillaries 12 may have different shapes, as illustrated for example below with reference to FIG. 3.

Figure 3:
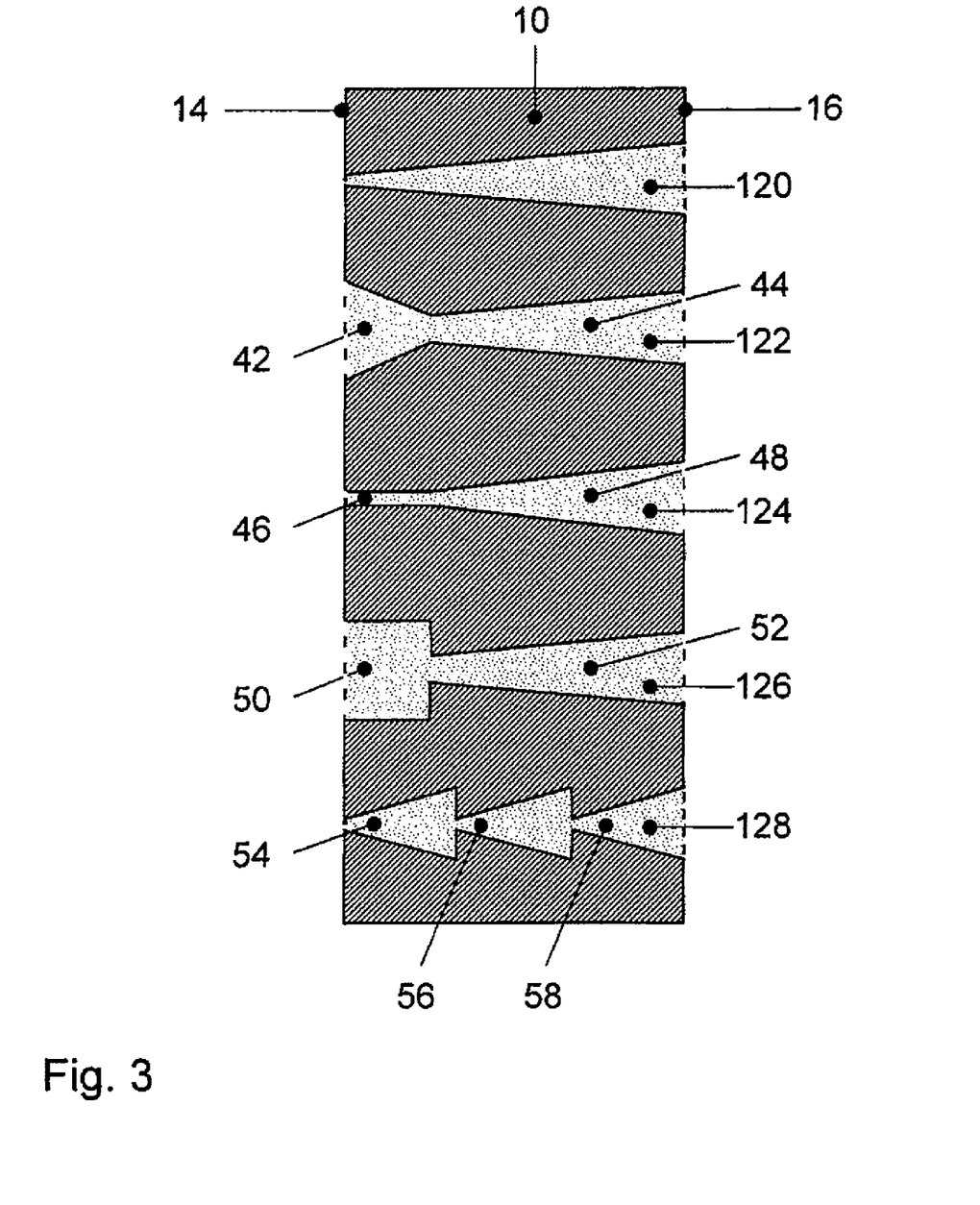
FIG. 3 shows a schematic illustration of a cross section of a capillary apparatus, according to one embodiment of the invention.

FIG. 3 is a schematic illustration of a section through a capillary apparatus, according to one embodiment of the invention. FIG. 3 may represent a capillary apparatus that may be used in the detector devices illustrated in FIGS. 1 and 2. The illustrated plane of section is substantially perpendicular to the first side 14 and the second side 16 of the capillary apparatus 10 and parallel to the capillaries 120, 122, 124, 126, 128 or to their longitudinal axes. However, it should be noted that the capillaries 120 to 128 do not have to be arranged and orientated exactly perpendicularly to the surfaces 14, 16 of the capillary apparatus 10.

A capillary apparatus 10 may have a large number of substantially the same capillaries. However, for the sake of illustration, FIG. 3 illustrates a single capillary apparatus 10 having five different capillaries 120, 122, 124, 126, 128. In one embodiment, deviating from FIG. 3, some or all of the capillaries 120 to 128 may taper from the first side 14 towards the second side 16.

Note that the capillaries 120 to 128 illustrated in FIG. 3 are provided to illustrate the cross-sectional area along the capillary measured parallel to the illustrated plane of section. However, the capillaries 120 to 128 of the capillary apparatus 10 may have a circular or elliptic cross section along their entire length or at least in sections. The dimension of the cross-sectional area measured perpendicularly to the plane of section illustrated in FIG. 3 may vary in substantially the same manner as the dimension of the cross-sectional area measured in the plane of section and illustrated in FIG. 3. Alternatively, only the cross-sectional area may vary according to the examples described below without the dimension which is measured parallel to the illustrated plane of section or the dimension which is perpendicular to the plane of section corresponding exactly to the examples.

As shown, the cross sections of the first three capillaries 120, 122, 124 change gradually. In contrast, the last two capillaries 126, 128 have steps where the cross section changes abruptly.

The first capillary 120 illustrated in FIG. 3 has its minimum cross-sectional area directly at the first side 14 of the capillary apparatus 10. The cross section or the cross-sectional area increases continuously from the first side 14 to the second side 16 of the capillary apparatus 10. In the case of a circular or elliptic cross section, the capillary 120 thus has the shape of a funnel or cone.

The minimum cross section or the minimum cross-sectional area of the second capillary 122 illustrated in FIG. 3 is spaced apart from the first side 14 of the capillary apparatus 10, but is closer to the first side 14 than to the second side 16. Starting from the first side 14 of the capillary apparatus 10, the cross section or the cross-sectional area of the capillary 122 decreases at first in a first section 42, and then subsequently increases in a second section 44 towards the second side 16. In the case of a circular or elliptic cross section, the capillary 122 thus has the shape of a double funnel with two funnel- or cone-shaped sections 42, 44 which open towards the two sides 14, 16 of the capillary apparatus 10.

The third capillary 124 illustrated in FIG. 3 has, at the first side 14 of the capillary apparatus 10, a first section 46 with a substantially constant cross section or a substantially constant cross-sectional area. This first section 46 is adjoined by a second section 48 in which the cross section or the cross-sectional area of the capillary 124 grows continuously and in the case of a circular or elliptic cross section preferably substantially in the shape of a funnel or cone.

The fourth capillary 126 illustrated in FIG. 3 has, similarly to the third capillary 124, a first section 50, adjoining the first side 14 of the capillary apparatus 10, with a substantially constant cross section or a substantially constant cross-sectional area. This first section 50 is adjoined by a second section 52 in which the cross section or the cross-sectional area continuously increases. In contrast to the third capillary 124, however, the fourth capillary 126 does not have the minimum cross section or the minimum cross-sectional area in the first section 50. Instead, the cross section or the cross-sectional area is larger or substantially larger and is reduced at the transition to the second section 52 in the manner of a step.

The fifth capillary 128 illustrated in FIG. 3 has a plurality of sections 54, 56, 58, between which the cross section or the cross-sectional area of the capillary 128 changes in each case in the manner of a step. Inside a section 54, 56, 58, the cross section or the cross-sectional area of the capillary 128 increases in each case in the direction from the first side 14 to the second side 16 of the capillary apparatus 10, only to subsequently decrease again in the manner of a step at the transition to the next section 56, 58. In the case of a circular or elliptic cross section, the capillary 128 thus has the shape of a plurality of funnels which are placed in a row in the same direction.

As described, different gases and in particular monatomic gases and molecular gases behave differently in the capillary apparatus 10. In particular, they pass through the capillary apparatus 10 or its capillaries at a different rate or velocity. Thus, referring again to the detector device illustrated in FIG. 1, the pressure measured by the pressure detector 20 may change depending on the composition of the gas mixture at various points in time. The change of the pressure over time (for example starting from an originally strongly reduced pressure or vacuum in the line 22) can thus be used to infer the composition of the gas mixture in the volume 18. Similarly, referring to the detector device illustrated in FIG. 2, a change in the pressure difference between the two sides 14, 16 of the capillary apparatus 10 over time can be used to infer the composition of the gas mixture. In one embodiment, the evaluation apparatus 28 may be configured to evaluate changes in measured pressure over a given time period. For example, the evaluation apparatus 28 may include a timing device.

The different throughflow rates of different gases at the capillary apparatus 10 can be used for filtering or enriching predetermined gas components. For example, helium or other noble gases may be extracted from any gas mixtures.

In one embodiment, for monatomic gases (e.g., helium or argon), the through-passage rates through the capillary apparatus 10 may be different from the first side 14 towards the second side 16 and from the second side 16 towards the first side 14. This difference may be due to the likelihood of the atoms of the monatomic gas passing from the first side 14 to the second side 16 of the capillary apparatus 10 being different than the other way around. Such a difference may result in a net gas flow, the direction of which may depend on the shape of the capillaries and the magnitude of which depends on the properties of the gas, wherein a significantly larger net gas flow may occur in monatomic gases than in molecular gases.

The result of such a net gas flow may be that, between the first side 14 and the second side 16 of the capillary apparatus 10, a pressure difference arises which can be detected, for example, by the pressure detector 20 of the detector device illustrated in FIG. 2. Since the net gas flow differs from gas to gas, the pressure difference can be used to infer the composition of the gas mixture. Accordingly, in one embodiment, the pressure difference (e.g., as measured by the pressure detector 20) after a given time period may be used to determine the composition of a gas mixture.

Figure 4:
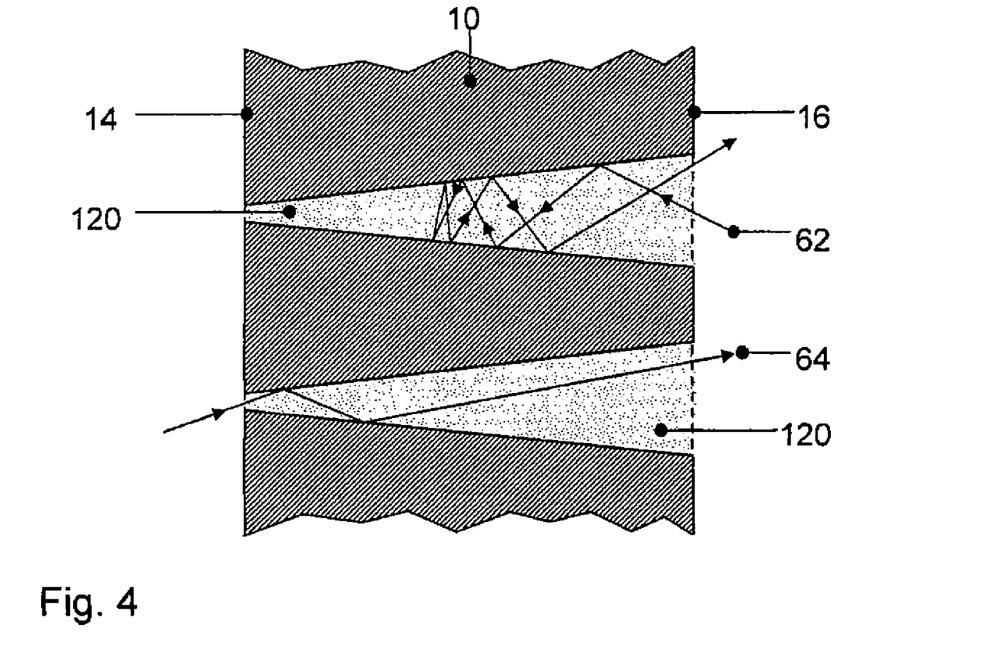
FIG. 4 shows a schematic illustration of a cross section of a capillary apparatus with particle paths, according to one embodiment of the invention.

The production of the net gas flow is described below by way of example with reference to the first capillary 120 illustrated in FIG. 3, which has the simplest structure from among the illustrated capillaries 120 to 128. Said capillary is illustrated again in FIG. 4 showing a detail of a capillary apparatus 10 with two capillaries 120 with simple funnel-shaped design, according to one embodiment of the invention. In the capillaries illustrated in FIG. 4, the paths 62, 64 of gas particles are shown. The net gas flow may occur when the mean free path of the gas particles is smaller or substantially smaller than the twentyfold diameter of the capillaries 120 perpendicular to their axes, and in particular when the mean free path is substantially the diameter of the capillaries 120. Under this condition, the paths are substantially ballistic or can be described by Newtonian mechanics. The kinematics of the reflection at the walls of the capillaries 120 is substantially described by the equation "angle of incidence=angle of deflection". This applies in the approximation of smooth walls.

In the example illustrated in the top portion of FIG. 4, a gas particle enters the capillary 120 from the second side 16 of the capillary apparatus 10. The path 62 of the gas particle indicates that, due to the angle between the walls of the capillary 120 which face each other, the angle between the path 62 and the axis of the capillary 120 increases with each reflection until it is approximately 90° and then decreases again. The gas particle thus leaves the capillary 120 on the second side 16 of the capillary apparatus 10. That is, the gas particle fails to pass through the entire length of the capillary apparatus 10.

In the example illustrated at the bottom in FIG. 4, the path 64 represents the path of a gas particle entering the capillary 120 from the first side 14 of the capillary apparatus 10. The path 64 indicates that the angle between the path 64 and the axis of the capillary 120 decreases with reach reflection and the gas particle exits the capillary 120 at the second side 16 of the capillary apparatus 10 without problems.

As illustrated by the paths 62, 64 of the gas particles which enter the capillary 120 from the second side 16 or from the first side 14, respectively, it can be seen that, at least under the abovementioned condition that the cross section of the capillary 120 is smaller than the mean free path of the gas particles or is comparable to it, a particle entering the capillary 120 from the second side 16 is very likely to leave the capillary apparatus 10 again on the same second side 16, whereas a particle entering the capillary 120 from the first side 14 is very likely to leave on the second side 16 of the capillary apparatus 10. The result of such a directional flow may produce a net gas flow from the first side 14 to the second side 16 of the capillary apparatus 10. Similarly, a net gas flow may result from the use of the other capillaries 122, 124, 126, 128 illustrated in FIG. 3.

It is obvious that an inverse arrangement, i.e. a capillary that tapers from the first side 14 towards the second side 16, has the reverse effect. A particle entering the capillary from the first side 14 then also very likely leaves the capillary apparatus 10 again on the first side. A particle entering the capillary from the second side 16 likewise very likely leaves on the first side 14.

Figure 5:
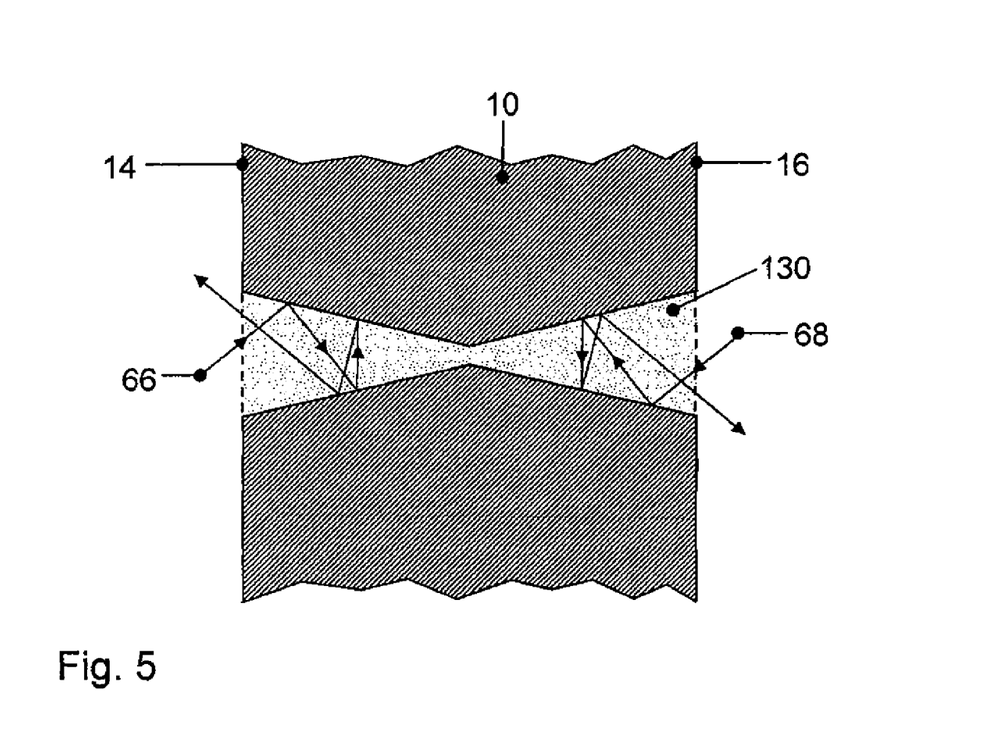
FIG. 5 shows a schematic illustration of a cross section of another capillary apparatus with particle paths, according to one embodiment of the invention.

FIG. 5 furthermore shows a capillary apparatus 10 with a symmetrical capillary 130, according to one embodiment of the invention. The symmetrical capillary 130 has the same diameter or the same cross-sectional area on both sides 14, 16 of the capillary apparatus 10 and tapers from both sides in the same manner up to a minimum diameter or a minimum cross-sectional area. The point in the capillary 130 with the minimum diameter or the minimum cross-sectional area is equally spaced apart from both sides 14, 16 of the capillary apparatus.

FIG. 5 also shows the paths 66, 68 of two particles. It can be seen from the paths 66, 68 which are illustrated by way of example that, in the case illustrated in FIG. 5, it is obviously just as likely for a particle that enters the capillary apparatus 10 on the first side 14 to leave the capillary apparatus 10 again on the first side 14 as it is for a particle that enters the capillary apparatus 10 on the second side 16 to leave the capillary apparatus 10 again on the second side 16.

The capillary apparatus illustrated in FIG. 5 may thus develop a blocking effect which can depend on the gas type. In particular, the blocking effect may depend on the mean free path of a given gas type. It is thus possible with respect to the illustrations of FIGS. 4 and 5 to achieve, due to the microscopic design of the capillaries of the capillary apparatus, a net gas flow in one or the other direction or also a blocking effect—which may depend on the gas type.

Figure 6:
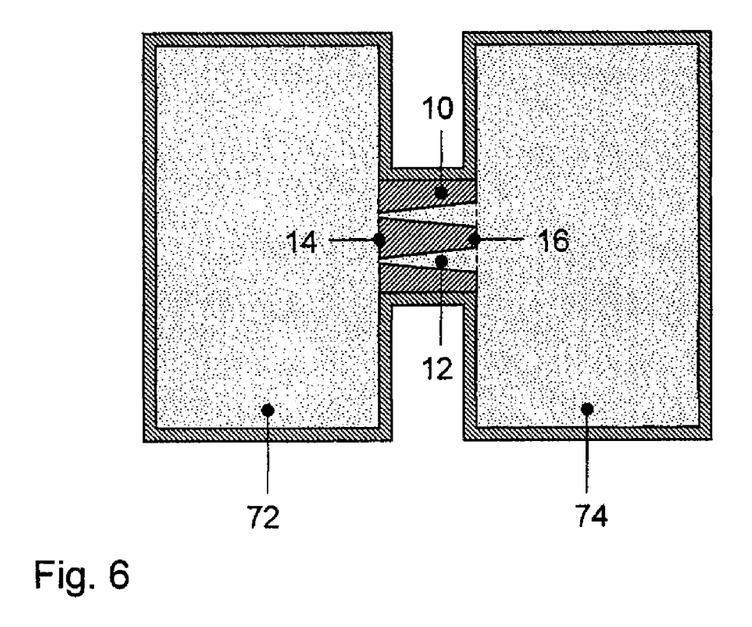
FIG. 6 shows a schematic illustration of a gas enrichment device, according to one embodiment of the invention.

Further, the capillary apparatuses 10 shown in FIGS. 3 to 5 may be suitable for extracting a predetermined gas, in particular a noble gas, from a gas mixture or at least to enrich the predetermined gas. FIG. 6 shows a gas enrichment device with a capillary apparatus 10, according to one embodiment of the invention. In this embodiment, the gas enrichment device comprises a first gas container 72 which is connected to the first side 14 of the capillary apparatus 10 and a second gas container 74 which is connected to the second side 16 of the capillary apparatus 10. Both the first and the second gas container 72, 74 can be connected in each case, as shown in FIG. 6, to the corresponding sides 14, 16 of the capillary apparatus 10 directly or via lines.

The first gas container 72 is filled with the gas mixture which contains the predetermined gas at a first concentration. Assume that the capillary apparatus 10 is configured such that the predetermined gas has a higher through-passage rate than other components of the gas mixture. Therefore, a gas mixture with a second concentration of the predetermined gas accumulates in the second gas container 74, with the second concentration being substantially higher than the first concentration.

In another embodiment, a continuously operating device may have a gas mixture supplied to the first gas container or directly to the first side 14 of the capillary apparatus 10 continuously or batch-wise through a gas supply line, while the predetermined gas (or a gas mixture with the enriched predetermined gas) is removed continuously or batch-wise from the second container or on the second side 16 of the capillary apparatus 10 through a gas discharge line.

Depending on the type and geometry of the capillaries 12, and further depending on the predetermined gas and the gas mixture from which the predetermined gas is meant to be extracted, the capillary apparatus 10 can also be configured in a reverse manner than that shown in FIG. 6. In this case, in deviation from FIG. 6, the first side 14 of the capillary apparatus 10 is connected to the second gas container 74 and the second side 16 of the capillary apparatus 10 is connected to the first gas container 72.

The capillary apparatus may be suitable for enriching or depleting noble gases such as helium or argon, which are monatomic gases. As described above, monatomic gases may behave differently in the capillaries 12 than molecular gases such as nitrogen or oxygen.

Figure 7:
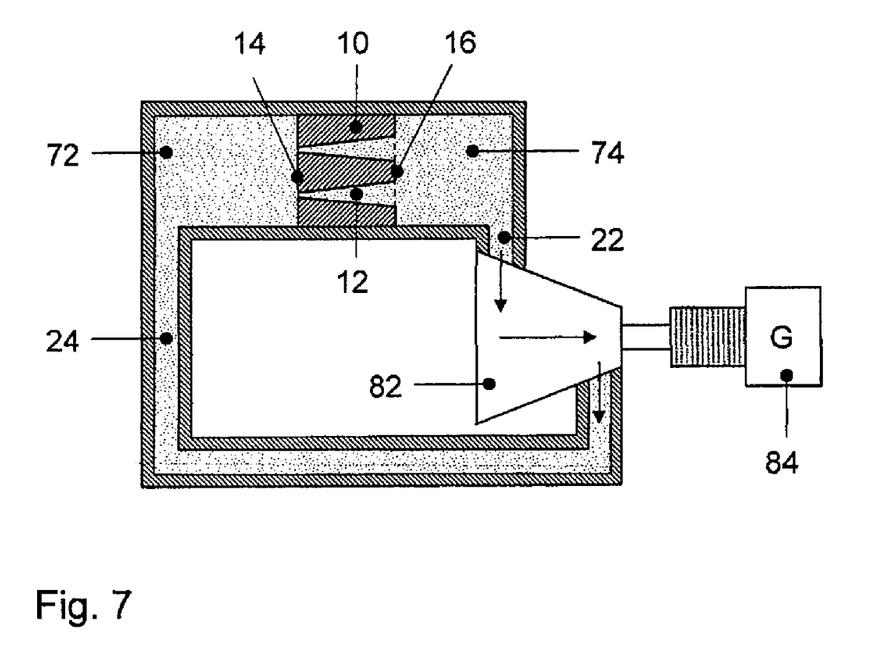
FIG. 7 shows a schematic illustration of a device, according to one embodiment of the invention.

In one embodiment, a net gas flow occurring on the capillary apparatus 10 may be utilized for doing mechanical work. FIG. 7 shows a device with a capillary apparatus 10 and a rotor 82. The shaft of the rotor 82 is connected to a converter 84. The second side 16 of the capillary apparatus 10 is connected to the front of the rotor 82, the first side 14 of the capillary apparatus 10 is connected to the rear of the rotor 82. The net gas flow occurring on the capillary apparatus 10 may thus be utilized to do mechanical work, which may then be converted into the movement of a pointer measuring instrument by the converter 84, for example. Alternatively, the mechanical power of the rotor 82 may be utilized to drive other apparatuses. Further, instead of driving the rotor 82, it is possible to use any other machine which outputs mechanical power when a gas is depressurized, for example a reciprocating engine.

Figure 8:
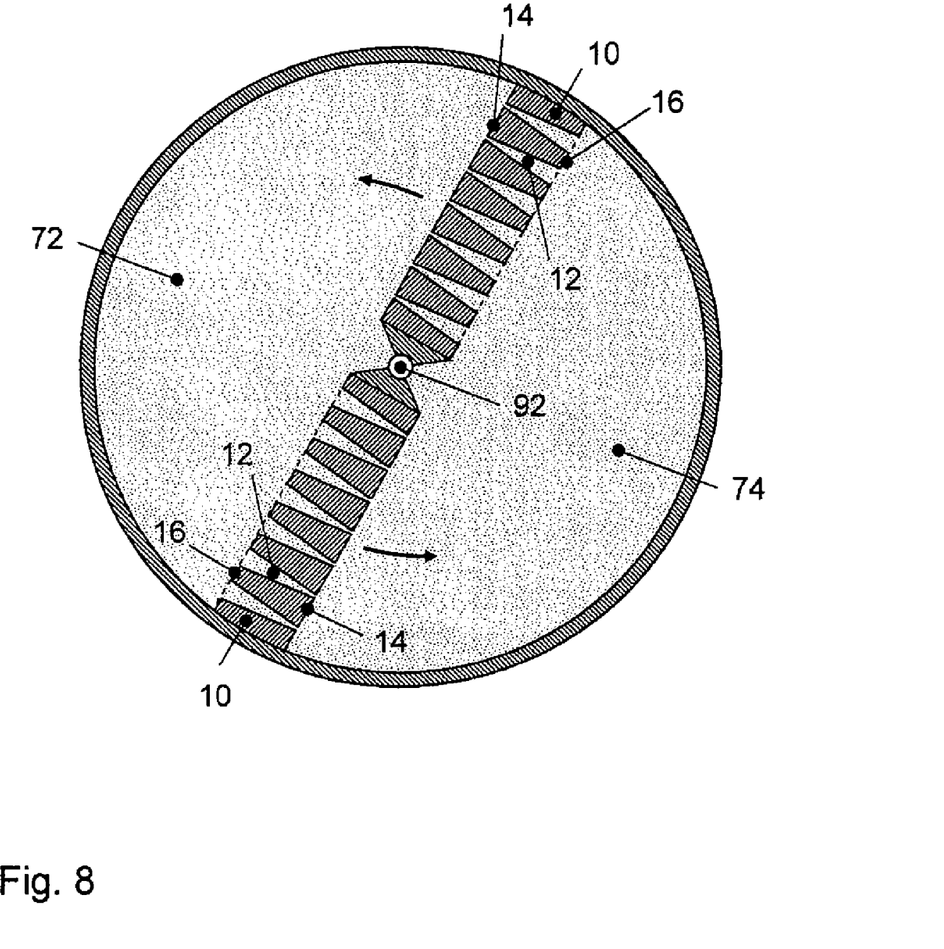
FIG. 8 shows a schematic illustration of another device, according to one embodiment of the invention.

FIG. 8 shows another application of capillary apparatuses 10, according to one embodiment of the invention. One or more capillary apparatuses 10, which may be as large as possible in terms of area, can be attached to a shaft 92. This shaft 92 is connected to a pointer (not illustrated). The net gas flow occurring at each capillary apparatus 10 produces a pressure difference, which is dependent on the gas composition, between the first side 14 and the second side 16. This pressure difference produces a torque which also depends on the gas composition. A spring (not illustrated) produces a counter-torque which depends on the rotation angle. The rotation angle, where the torque produced by the capillary apparatuses and the counter-torque produced by the spring are of the same magnitude, and thus the position of the pointer are therefore—in a first approximation linear—functions of the gas composition or of a partial pressure of a predetermined gas in a gas mixture. Alternatively, mechanical power is taken via the shaft 92, which power can be used for example to drive a generator or another device.

In all of the above exemplary embodiments, the lengths of the capillaries 12, 120, 122, 124, 126, 128, 130 or the lengths of their sections 44, 48, 52, 54, 56, 58, the tapering angle, and the ratio between the minimum diameter of a capillary and the mean free path of a gas particle, may be matched preferably to the temperature, the pressure and the predetermined gas whose presence is meant to be detected by the detector device or which is meant to be enriched.

In all of the above exemplary embodiments, a different effect (for example, an increased pressure or partial pressure or an increased pressure or partial pressure difference) may be achieved by exposing the device to a pressure oscillation. Such a pressure oscillation can, for example, be sound acting on the device. Embodiments of the invention can thus also be used in particular to convert sound energy into mechanical energy.

What is claimed is:

1. A device for passing through a gas mixture containing a predetermined gas with a mean free path, comprising:
a capillary apparatus with one or more capillaries connecting a first side of the capillary apparatus to a second side of the capillary apparatus, wherein:
each capillary tapers from one side towards the other side of the capillary apparatus at least in one of a first section and a second section;
a cross section of each capillary changes abruptly between the first section and the second section, and
a minimum cross section of each capillary, in at least one direction, has a dimension that is the same order of magnitude as the mean free path of the predetermined gas.

2. The device as claimed in claim 1, further comprising a gas line, which is connected to the first side of the capillary apparatus, for supplying the gas mixture to the first side of the capillary apparatus.

3. The device as claimed in claim 1, wherein the cross-sectional area of the capillary increases from one side to the other side of the capillary apparatus.

4. The device as claimed in claim 1, wherein the cross-sectional area of the capillary increases steadily over a length which is larger than half the length of the capillary.

5. The device as claimed in claim 1, wherein the capillary has any of a substantially circular and elliptic cross section.

6. The device as claimed in claim 1, wherein the capillary has a substantially funnel-shaped or cone-shaped section.

7. The device as claimed in claim 1, wherein the minimum cross section of the capillary is at most twice as large at least in one direction as the mean free path of the predetermined gas.

8. The device as claimed in claim 1, wherein the capillary is configured such that atomic gases pass through the capillary at a different rate than molecular gases.

9. The device as claimed in claim 1, wherein the capillary is configured such that the predetermined gas passes through the capillary at a different rate than other components of the gas mixture.

10. The device as claimed in claim 1, wherein the capillary is configured such that atomic gases pass from the first side to the second side of the capillary apparatus through the capillary at a different rate than in the other direction.

11. The device as claimed in claim 1, wherein the capillary is configured such that the predetermined gas passes from the first side to the second side of the capillary apparatus through the capillary at a different rate than in the other direction.

12. The device as claimed in claim 1, wherein the capillary apparatus has a plurality of capillaries which have the same properties and connect the first side of the capillary apparatus to the second side of the capillary apparatus.

13. The device as claimed in claim 1, further comprising a timing device for timing a flow of the predetermined gas.

14. A detector device for qualitatively or quantitatively detecting the presence of a predetermined gas in a gas mixture, comprising:
a capillary apparatus with one or more capillaries connecting a first side of the capillary apparatus to a second side of the capillary apparatus, wherein each capillary tapers from one side towards the other side of the capillary apparatus at least in sections;
a pressure detector connected to the second side; and
an evaluation apparatus which is connected to the pressure detector for receiving a measurement signal from the pressure detector, wherein the evaluation apparatus is configured to generate an output signal on the basis of the measurement signal which indicates at least one of: (i) the presence of the predetermined gas in the gas mixture at a minimum concentration, (ii) the partial pressure of the predetermined gas, (iii) the proportion by volume of the predetermined gas, and (iv) the proportion by material of the predetermined gas.

15. The detector device as claimed in claim 14, further comprising a gas line, which is connected to the first side of the capillary apparatus, for supplying the gas mixture to the first side of the capillary apparatus.

16. The detector device apparatus as claimed in claim 14, wherein the pressure detector is a differential pressure detector for detecting a pressure difference, and wherein the pressure detector is connected to the first side of the capillary apparatus in order to detect a pressure difference between the first side and the second side of the capillary apparatus.

17. A gas enrichment device for extracting a predetermined gas from a first gas mixture or for enriching the predetermined gas, comprising:
a capillary apparatus with one or more capillaries connecting a first side of the capillary apparatus to a second side of the capillary apparatus, wherein each capillary tapers from one side towards the other side of the capillary apparatus at least in sections, the capillary apparatus being configured such that the predetermined gas has a higher through-passage rate than other components of the first gas mixture;
a first gas container that is connected to the first side of the capillary apparatus and is filled with the first gas mixture which contains the predetermined gas at a first concentration; and
a second gas container that is connected to the second side of the capillary apparatus and is filled with a second gas mixture which contains the predetermined gas at a second concentration, the second concentration being substantially greater than the first concentration.

18. A device for generating mechanical power, comprising:
- a capillary apparatus with one or more capillaries connecting a first side of the capillary apparatus to a second side of the capillary apparatus, wherein each capillary tapers from one side towards the other side of the capillary apparatus at least in sections; and
- a device for depressurizing gas and for generating mechanical power, wherein an entry side of the device for depressurizing gas is connected to one of the sides of the capillary apparatus, and wherein an exit side of the device for depressurizing gas is connected to the other side of the capillary apparatus.

19. A device for inducing a rotational movement, comprising:
- a shaft;
- a capillary apparatus with one or more capillaries connecting a first side of the capillary apparatus to a second side of the capillary apparatus, wherein each capillary tapers from one side towards the other side of the capillary apparatus at least in sections;
- a pointer which is connected to the shaft and indicates its rotation angle; and
- a spring which is connected to the shaft and exerts a torque on it which is dependent on the rotation angle, wherein the position of the pointer indicates at least one of: (i) a gas composition, and a partial pressure of a predetermined gas in a gas mixture.

20. A method for passing through components of a first gas mixture, comprising:
- supplying the first gas mixture which contains a predetermined gas at a first concentration to a first side of a capillary apparatus, the capillary apparatus comprising one or more capillaries that connect the first side of the capillary apparatus to a second side of the capillary apparatus, wherein each capillary is tapered in at least one section, the capillary apparatus being configured such that the predetermined gas has a higher through-passage rate than other components of the first gas mixture; and
- discharging a second gas mixture which contains the predetermined gas at a second concentration, the second concentration being substantially greater than the first concentration.

* * * * *